United States Patent
Kuga

(10) Patent No.: US 9,734,621 B2
(45) Date of Patent: Aug. 15, 2017

(54) ULTRASONIC DIAGNOSTIC APPARATUS, IMAGE PROCESSING APPARATUS, AND IMAGE PROCESSING METHOD

(71) Applicant: Toshiba Medical Systems Corporation, Otawara-shi (JP)

(72) Inventor: Itsuki Kuga, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 290 days.

(21) Appl. No.: 14/607,131

(22) Filed: Jan. 28, 2015

(65) Prior Publication Data

US 2015/0139521 A1    May 21, 2015

Related U.S. Application Data

(63) Continuation of application No. PCT/JP2013/074764, filed on Sep. 12, 2013.

(30) Foreign Application Priority Data

Sep. 12, 2012 (JP) ................................. 2012-200707

(51) Int. Cl.
*G06T 15/08* (2011.01)
*A61B 8/14* (2006.01)
(Continued)

(52) U.S. Cl.
CPC .............. *G06T 15/08* (2013.01); *A61B 8/145* (2013.01); *A61B 8/466* (2013.01); *A61B 8/483* (2013.01);
(Continued)

(58) Field of Classification Search
CPC ............................. G06T 2200/16; G06T 15/08
See application file for complete search history.

(56) References Cited

U.S. PATENT DOCUMENTS 6,914,599 B1   7/2005   Rowe et al.
7,109,989 B2   9/2006   Bissell et al.
(Continued)

FOREIGN PATENT DOCUMENTS

JP   2000-20728 A   1/2000
JP   2001-76180 A   3/2001
(Continued)

OTHER PUBLICATIONS

Managuli, Ravi, et al. "Volume rendering algorithms for three-dimensional ultrasound imaging: image quality and real-time performance analysis." Ultrasonics Symposium (IUS), 2009 IEEE International. IEEE, 2009.*

(Continued)

*Primary Examiner* — Stephen R Koziol
*Assistant Examiner* — Raphael Schwartz
(74) *Attorney, Agent, or Firm* — Oblon, McClelland, Maier & Neustadt, L.L.P.

(57) ABSTRACT

An ultrasonic diagnostic apparatus according to an embodiment includes a rendering controller, a detector, and a voxel data generator. The rendering controller divides three-dimensional data constituted by voxel data into a plurality of slice regions, rearranges the slice regions based on a sight line direction in which the voxel data is observed, and performs volume rendering on the voxel data in which the slice regions have been rearranged so as to generate image data. The detector detects image quality information indicating image quality of image data that is generated by the rendering controller. The voxel data generator rearranges the voxel data constituting the three-dimensional data based on the image quality information detected by the detector based on the sight line direction.

7 Claims, 10 Drawing Sheets

(51) Int. Cl.
*A61B 8/00* (2006.01)
*A61B 8/08* (2006.01)
*G06T 7/00* (2017.01)

(52) U.S. Cl.
CPC ............ *A61B 8/523* (2013.01); *G06T 7/0012* (2013.01); *A61B 8/5207* (2013.01); *G06T 2207/10136* (2013.01); *G06T 2210/41* (2013.01)

(56) References Cited

U.S. PATENT DOCUMENTS

| 2008/0024515 A1* | 1/2008 | Yang ........................ G06T 15/06 345/592 |
| 2008/0129732 A1* | 6/2008 | Johnson ................ G06T 7/0002 345/424 |
| 2012/0065512 A1 | 3/2012 | Hamada et al. |

FOREIGN PATENT DOCUMENTS

| JP | 2003-530176 A | 10/2003 |
| JP | 2006-204621 A | 8/2006 |
| JP | 2012-81257 A | 4/2012 |

OTHER PUBLICATIONS

International Search Report issued Oct. 8, 2013 for PCT/JP2013/074764 filed on Sep. 12, 2013 with English Translation.
Written Opinion issued Oct. 8, 2013 for PCT/JP2013/074764 filed on Sep. 12, 2013.

* cited by examiner

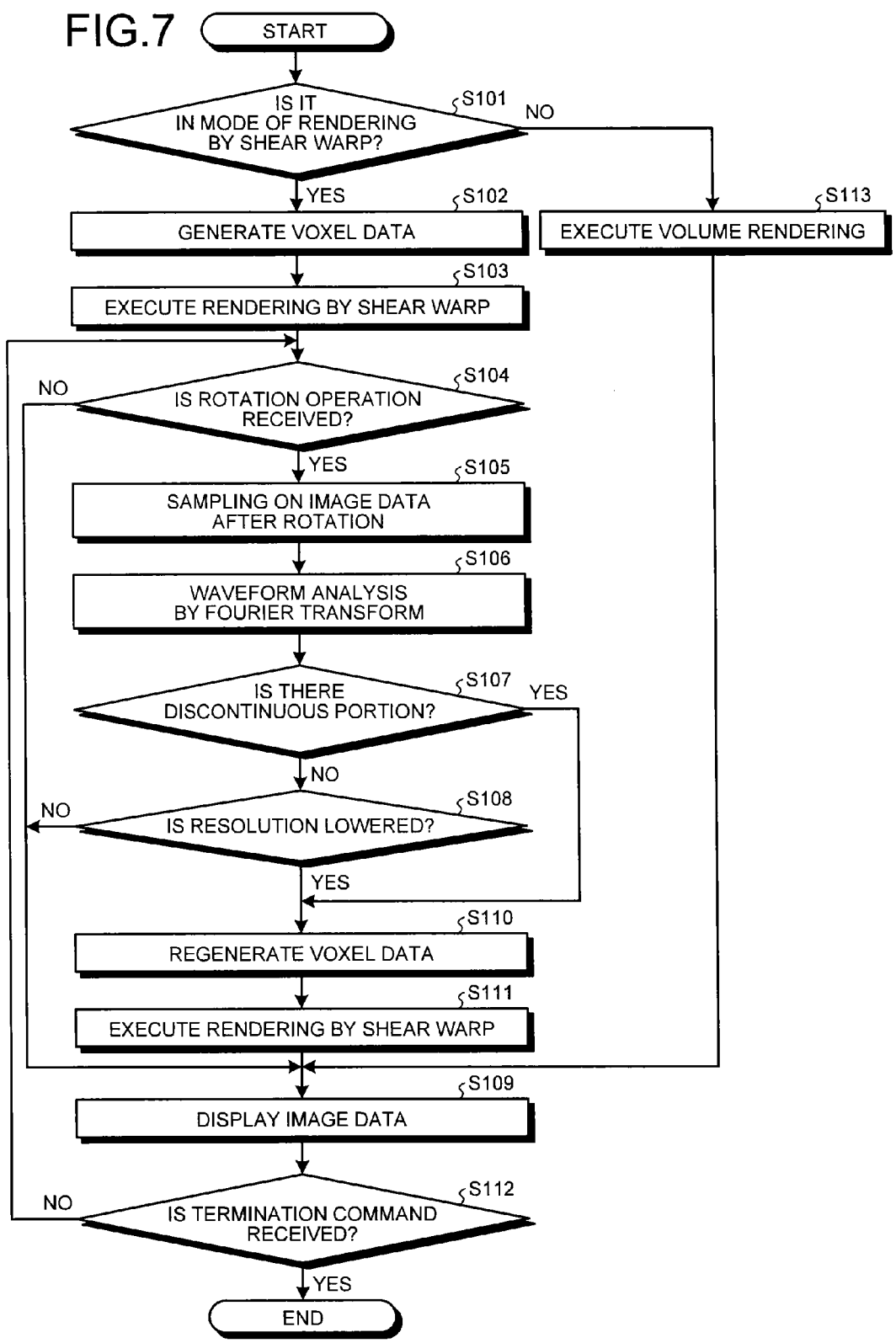

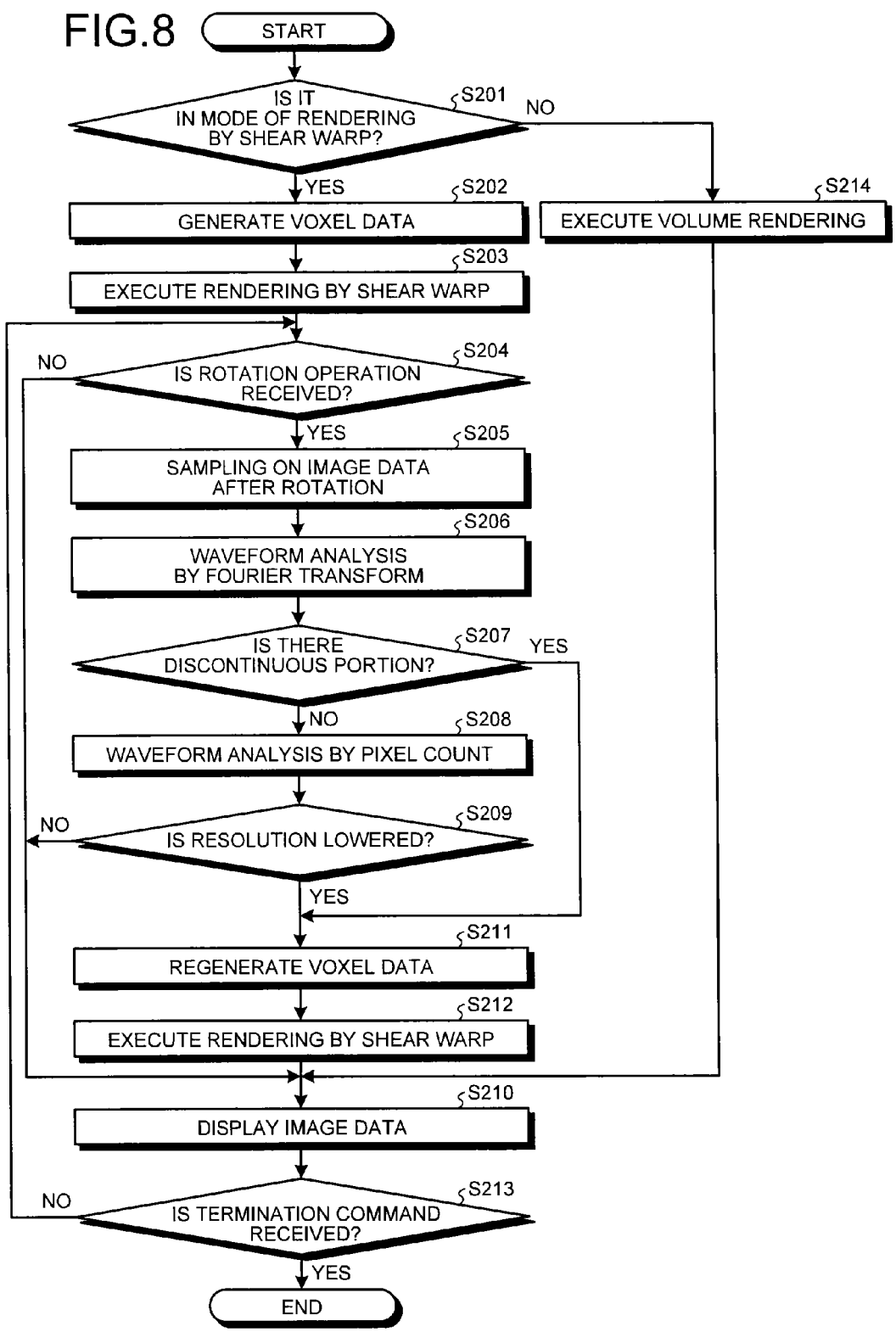

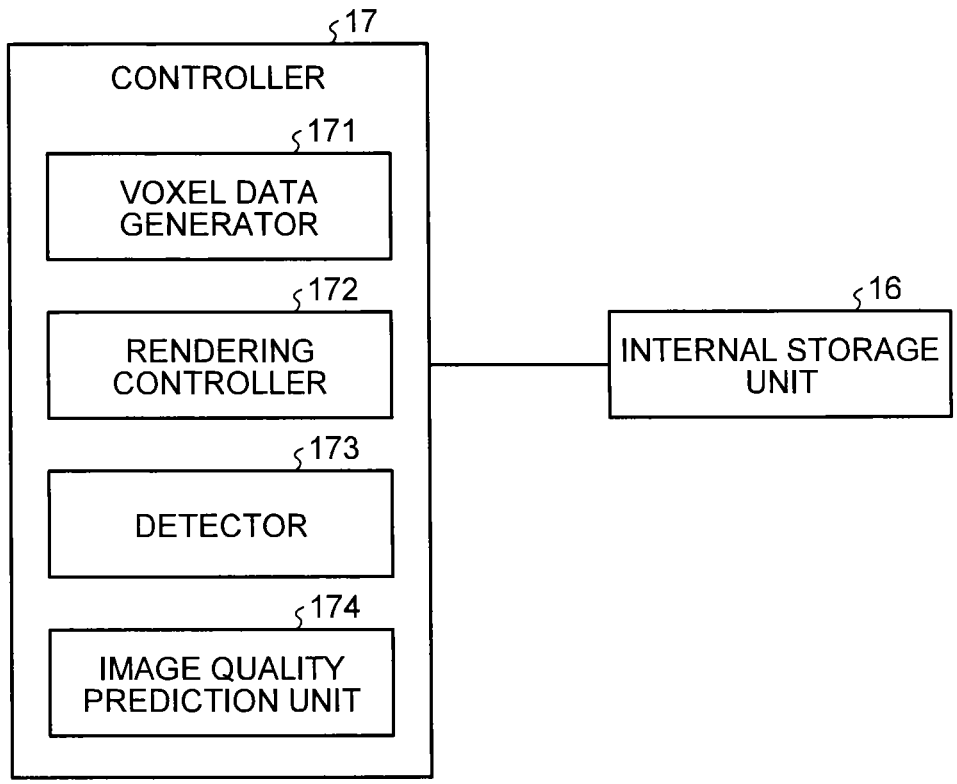

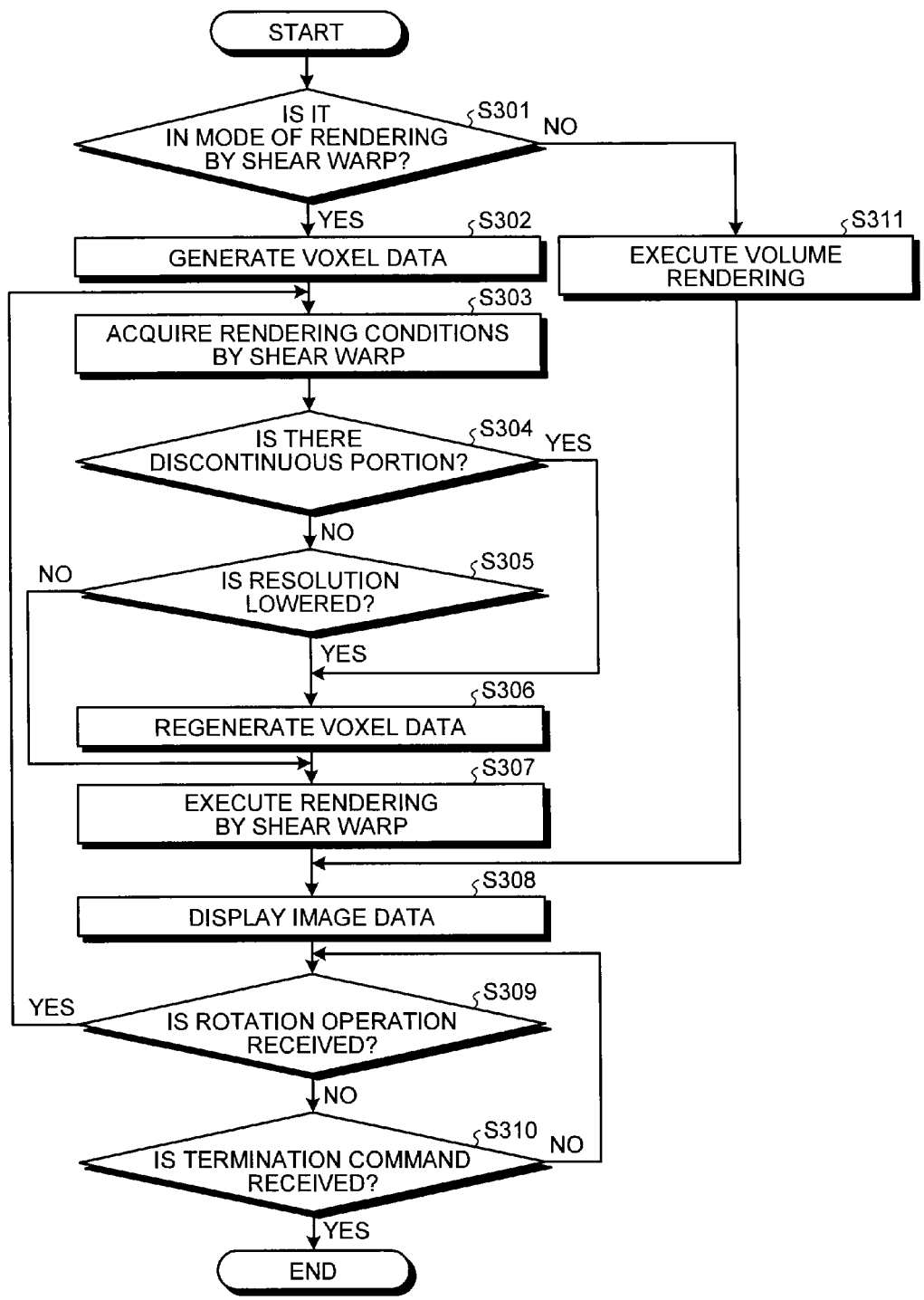

ULTRASONIC DIAGNOSTIC APPARATUS, IMAGE PROCESSING APPARATUS, AND IMAGE PROCESSING METHOD

CROSS-REFERENCE TO RELATED APPLICATIONS

This application is a continuation of International Application No. PCT/JP2013/074764, filed on Sep. 12, 2013 which claims the benefit of priority of the prior Japanese Patent Application No. 2012-200707, filed on Sep. 12, 2012, the entire contents of which are incorporated herein by reference.

FIELD

Embodiments described herein relate generally to an ultrasonic diagnostic apparatus, an image processing apparatus, and an image processing method.

BACKGROUND

A conventional ultrasonic diagnostic apparatus collects three-dimensional data (volume data) by using a two-dimensional (2D) array probe and a mechanical four-dimensional (4D) probe and displays an ultrasonic image obtained by performing volume rendering on the collected volume data. When the ultrasonic image is displayed, the ultrasonic diagnostic apparatus can display an ultrasonic image obtained by performing volume rendering on voxel data. Note that the voxel data is obtained by converting coordinates of the volume data into those in a three-dimensional Cartesian coordinate system constituted by XYZ coordinates.

A shear warp method has been known as a method of performing volume rendering at a high speed in recent years. The shear warp method is a rendering method using the above-mentioned voxel data. With the shear warp method, pieces of sliced voxel data are rearranged in accordance with change (rotation) in the sight line direction so as to perform the volume rendering at a high speed. With the above-mentioned technique, it is difficult to prevent image quality from being lowered efficiently in some cases.

BRIEF DESCRIPTION OF THE DRAWINGS

FIG. 7 is a flowchart illustrating procedures of processing by the ultrasonic diagnostic apparatus in the first embodiment;

FIG. 8 is a flowchart illustrating procedures of processing by an ultrasonic diagnostic apparatus according to a second embodiment;

FIG. 9 is a drawing illustrating an example of a configuration of a controller according to a third embodiment;

FIG. 10 is a table illustrating an example of prediction information that is stored by an internal storage unit in the third embodiment; and FIG. 11 is a flowchart illustrating procedures of processing by the ultrasonic diagnostic apparatus in the third embodiment.

DETAILED DESCRIPTION

According to embodiment, an ultrasonic diagnostic apparatus comprising a rendering unit, a detector and voxel data generator. The rendering unit that divides three-dimensional data constituted by voxel data into a plurality of slice regions, rearranges the slice regions based on a sight line direction in which the voxel data is observed, and performs volume rendering on the voxel data in which the slice regions have been rearranged so as to generate image data. The detector that detects image quality information indicating image quality of image data that is generated by the rendering unit. The voxel data generator that rearranges the voxel data constituting the three-dimensional data in accordance with the image quality information detected by the detector based on the sight line direction.

Figure 1:
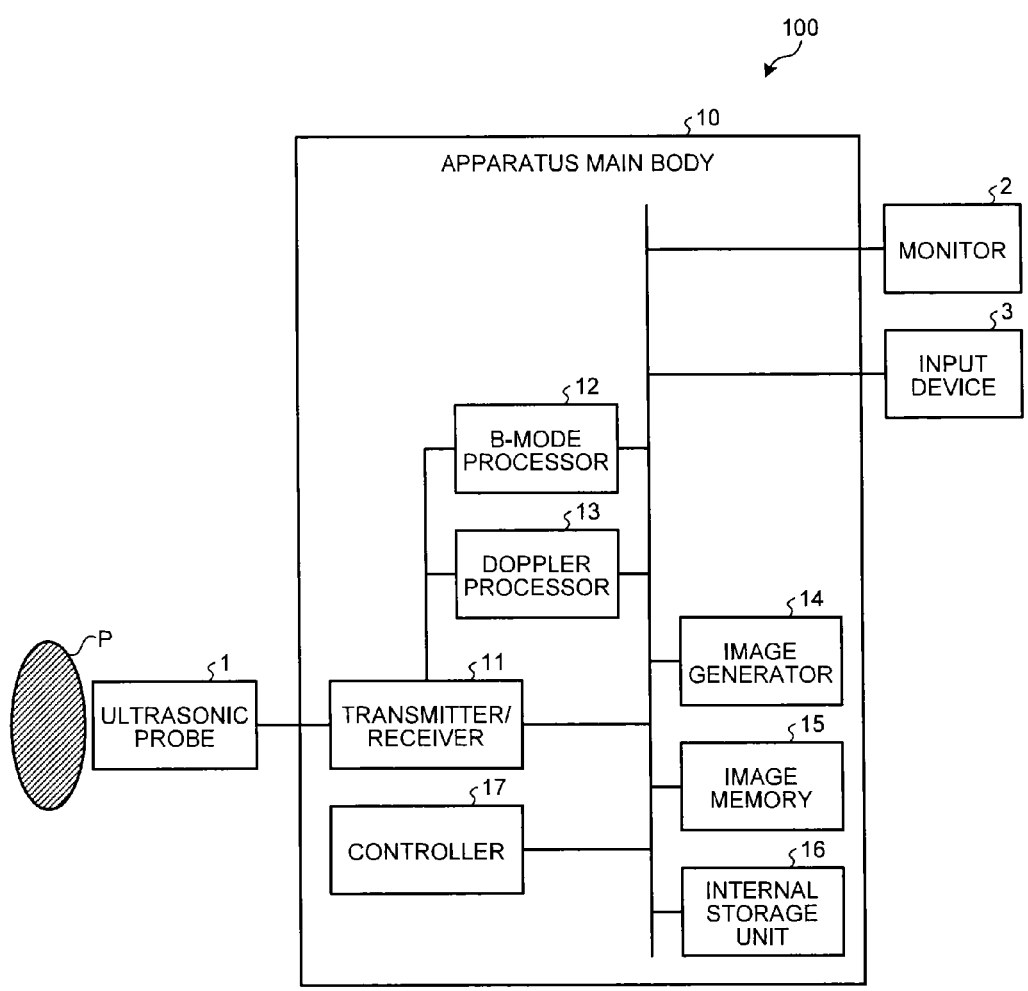
FIG. 1 is a drawing for explaining an overall configuration of an ultrasonic diagnostic apparatus according to a first embodiment.

First, described is a configuration of an ultrasonic diagnostic apparatus according to the embodiment. FIG. 1 is a drawing for explaining an overall configuration of an ultrasonic diagnostic apparatus 100 according to the first embodiment. As illustrated in FIG. 1, the ultrasonic diagnostic apparatus 100 in the first embodiment includes an ultrasonic probe 1, a monitor 2, an input device 3, and an apparatus main body 10.

The ultrasonic probe 1 includes a plurality of piezoelectric transducer elements and the piezoelectric transducer elements generate ultrasonic waves based on a driving signal that is supplied from a transmitter/receiver 11 included in the apparatus main body 10, which will be described later. The ultrasonic probe 1 receives reflection waves from a subject P and converts the reflection waves into an electric signal. The ultrasonic probe 1 includes a matching layer provided on the piezoelectric transducer elements and a backing material that prevents the ultrasonic waves from being transmitted backward from the piezoelectric transducer elements. The ultrasonic probe 1 is connected to the apparatus main body 10 in a detachable manner.

When the ultrasonic probe 1 transmits ultrasonic waves to the subject P, the transmitted ultrasonic waves are reflected by discontinuous surfaces of acoustic impedance in body tissues of the subject P one after another. Then, the plurality of piezoelectric transducer elements included in the ultrasonic probe 1 receives the ultrasonic waves as reflection wave signals. The amplitudes of the received reflection wave signals depend on differences in the acoustic impedance between the discontinuous surfaces by which the ultrasonic waves are reflected. The reflection wave signals when the transmitted ultrasonic wave pulses are reflected by surfaces of moving blood flows, cardiac walls, and the like receive frequency shift depending on velocity components of the moving members in the ultrasonic wave transmission direction due to the Doppler effect.

The ultrasonic probe 1 in the embodiment is an ultrasonic probe that can scan the subject P with ultrasonic waves two-dimensionally and can scan the subject P three-dimensionally. To be specific, the ultrasonic probe 1 in the embodiment is a mechanical scan probe that makes the plurality of piezoelectric transducer elements for scanning the subject P two-dimensionally swings at a predetermined angle (swing angle) so as to scan the subject P three-dimensionally. Alternatively, the ultrasonic probe 1 in the embodiment is a two-dimensional ultrasonic probe that can scan the subject P with ultrasonic waves three-dimensionally by arranging the plurality of piezoelectric transducer elements in a matrix manner. The two-dimensional ultrasonic probe focuses and transmits the ultrasonic waves so as to scan the subject P two-dimensionally.

The monitor 2 displays a graphical user interface (GUI) through which an operator of the ultrasonic diagnostic apparatus 100 inputs setting requests of various types by using the input device 3 and displays an ultrasonic image and the like generated by the apparatus main body 10. For example, the monitor 2 displays a rendering image generated under control by a controller 17, which will be described later.

The input device 3 includes a track ball, a switch, a dial, and a touch command screen. The input device 3 receives setting requests of various types from the operator of the ultrasonic diagnostic apparatus 100 and transfers the received setting requests of various types to the apparatus main body 10. For example, the input device 3 receives a rotation operation for changing a direction of a volume rendering image displayed on the monitor 2 and transfers information of the received rotation operation (for example, rotation by 45 degrees in the right direction) to the controller 17.

The apparatus main body 10 is an apparatus that generates an ultrasonic image based on reflection waves received by the ultrasonic probe 1. To be specific, the apparatus main body 10 in the embodiment is an apparatus that can generate a three-dimensional ultrasonic image (volume data) based on three-dimensional reflection wave data received by the ultrasonic probe 1. As illustrated in FIG. 1, the apparatus main body 10 includes the transmitter/receiver 11, a B-mode processor 12, a Doppler processor 13, an image generator 14, an image memory 15, an internal storage unit 16, and the controller 17.

The transmitter/receiver 11 includes a trigger generation circuit, a delay circuit and a pulsar circuit, and supplies a driving signal to the ultrasonic probe 1. The pulsar circuit repeatedly generates a rate pulse for forming transmission ultrasonic waves at a predetermined rate frequency. The delay circuit gives a delay time for each piezoelectric transducer element that is necessary for focusing the ultrasonic waves generated by the ultrasonic probe 1 in a beam form and determining a transmission directional characteristic thereof to each rate pulse generated by the pulsar circuit. The trigger generation circuit applies a driving signal (driving pulse) to the ultrasonic probe 1 at a timing based on the rate pulse. That is to say, the delay circuit adjusts the transmission direction from the surface of each piezoelectric transducer element arbitrarily by changing the delay time that is given to each rate pulse.

The transmitter/receiver 11 has a function of being capable of changing a transmission frequency, a transmission driving voltage, and the like instantaneously in order to execute a predetermined scan sequence based on a direction by the controller 17, which will be described later. In particular, the transmission driving voltage is changed by a linear amplifier-type oscillating circuit capable of switching the value instantaneously or a mechanism of switching a plurality of power supply units electrically.

Furthermore, the transmitter/receiver 11 includes an amplifier circuit, an analog-to-digital (A/D) converter, and an adder. The transmitter/receiver 11 performs various pieces of processing on the reflection wave signal received by the ultrasonic probe 1 so as to generate reflection wave data. The amplifier circuit amplifies the reflection wave signal for each channel and performs gain correction processing. The A/D converter A/D-converts the reflection wave signal on which gain correction has been performed and gives a delay time necessary for determining a reception directional characteristic to the digital data. The adder performs addition processing on the reflection wave signal processed by the A/D converter so as to generate reflection wave data. The addition processing by the adder emphasizes a reflection component from the direction in accordance with the reception directional characteristic of the reflection wave signal.

In this manner, the transmitter/receiver 11 controls the transmission directional characteristic and the reception directional characteristic in transmission and reception of the ultrasonic waves. The transmitter/receiver 11 in the embodiment causes the ultrasonic probe 1 to transmit three-dimensional ultrasonic wave beams to the subject P so as to generate three-dimensional reflection wave data from the three-dimensional reflection wave signal received by the ultrasonic probe 1.

The B-mode processor 12 receives the reflection wave data from the transmitter/receiver 11, and performs logarithmic amplification, envelope detection processing, and the like so as to generate data (B-mode data) in which a signal intensity is expressed by brightness. The B-mode processor 12 changes a detection frequency so as to change a frequency bandwidth to be imaged. Furthermore, the B-mode processor 12 can perform detection processing with two detection frequencies on one reflection wave data in parallel.

The Doppler processor 13 performs frequency analysis on velocity information from the reflection wave data received from the transmitter/receiver 11. Then, the Doppler processor 13 extracts blood flow, tissues, and contrast agent echo components with the Doppler effect so as to generate data (Doppler data) obtained by extracting moving member information such as an average velocity, dispersion, and power for multiple points.

The B-mode processor 12 and the Doppler processor 13 in the embodiment can perform processing on both the two-dimensional reflection wave data and the three-dimensional reflection wave data. That is to say, the B-mode processor 12 in the embodiment can generate three-dimensional B-mode data from the three-dimensional reflection wave data. Furthermore, the Doppler processor 13 in the embodiment can generate three-dimensional Doppler data from the three-dimensional reflection wave data.

The image generator 14 generates an ultrasonic image from pieces of data generated by the B-mode processor 12 and the Doppler processor 13. That is to say, the image generator 14 generates a B-mode image in which the intensity of the reflection waves is expressed by brightness from the B-mode data generated by the B-mode processor 12. To be specific, the image generator 14 generates a three-dimensional B-mode image from the three-dimensional B-mode data generated by the B-mode processor 12.

Furthermore, the image generator 14 generates a color Doppler image as an average velocity image, a dispersion image, a power image, or a combination image thereof indicating moving member information from the Doppler data generated by the Doppler processor 13. To be specific, the image generator 14 generates a three-dimensional color Doppler image from the three-dimensional Doppler data generated by the Doppler processor 13. Note that the three-dimensional B-mode image and the three-dimensional color Doppler image generated by the image generator 14 are referred to as "volume data" collectively.

The image generator 14 can generate images of various types for displaying the generated volume data on the monitor 2. To be specific, the image generator 14 can generate an MPR image and a rendering image from the volume data.

That is to say, the ultrasonic probe 1 performs three-dimensional scan with ultrasonic waves on a scanning site of the subject P, so that the transmitter/receiver 11 generates three-dimensional data. Then, the image generator 14 generates, as the image for displaying volume data on the monitor 2, an MPR image on three perpendicular intersecting planes, a rendering image when a contact surface of the ultrasonic probe 1 with the subject P is set as a viewpoint, or a rendering image when an arbitrary place is set as the viewpoint based on a direction from the operator, for example.

The image generator 14 generates a rendering image from voxel data obtained by converting coordinates of the volume data into those in a three-dimensional Cartesian coordinate system constituted by XYZ coordinates. For example, the image generator 14 generates the rendering image from the voxel data by using shear warp.

The image memory 15 is a memory that stores therein the ultrasonic image generated by the image generator 14. The image memory 15 can also store therein pieces of data generated by the B-mode processor 12 and the Doppler processor 13.

The internal storage unit 16 stores therein various pieces of data such as control programs for performing transmission and reception of ultrasonic waves, image processing, and display processing; diagnosis information (for example, patient IDs and findings by physicians); diagnostic protocols; and various types of body marks. The internal storage unit 16 is also used for keeping images stored by the image memory 15 if necessary, for example. The internal storage unit 16 stores therein prediction information for predicting image quality of a rendering image that is generated by the shear warp. The prediction information will be described in detail later.

The controller 17 is a control processor (central processing unit (CPU)) for executing a function as an information processing device (calculator) and controls the overall processing of the ultrasonic diagnostic apparatus 100. To be specific, the controller 17 controls the pieces of processing by the transmitter/receiver 11, the B-mode processor 12, the Doppler processor 13, and the image generator 14 based on various types of setting requests input from an operator through the input device 3 and various types of control programs and various pieces of data loaded from the internal storage unit 16. The controller 17 controls to display the ultrasonic image stored in the image memory 15, various types of images stored in the internal storage unit 16, the GUI for performing processing by the image generator 14, a processing result by the image generator 14, or the like on the monitor 2.

Hereinabove, described has been the overall configuration of the ultrasonic diagnostic apparatus 100 in the first embodiment. With the configuration, the ultrasonic diagnostic apparatus 100 in the first embodiment is configured so as to suppress lowering of image quality by processing by the controller 17, which will be described in detail.

Figure 2A:
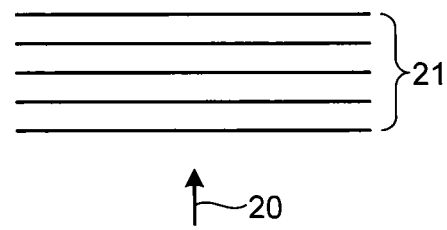
FIGS. 2A to 2C are drawings for explaining an example of a problem relating to a conventional technique.
Figure 2B:
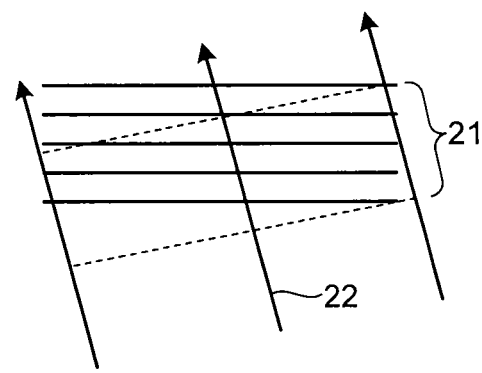
Figure 2C:
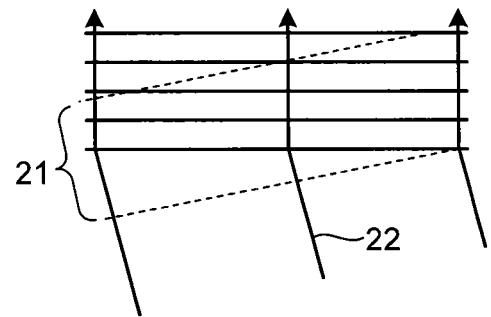

First, described is the conventional technique, in particular, the case where image quality is lowered on the rendering image that is generated by using the shear warp. FIGS. 2A to 2C are drawings for explaining an example of a problem relating to the conventional technique. FIGS. 2A to 2C illustrate voxel data obtained by converting coordinates of volume data into those in the three-dimensional Cartesian coordinate system when seen from the above. That is to say, each of solid lines as illustrated in FIGS. 2A to 2C indicates slice data generated from the volume data.

For example, in rendering of generating a rendering image from the voxel data, as illustrated in FIG. 2A, a rendering image is generated from the voxel data in a clipping plane thickness 21 from a sight line direction 20. That is to say, in FIG. 2A, when rendering is performed from the sight line direction 20, rendering by using the voxel data for five slices is performed.

As illustrated in FIG. 2B, when the sight line direction is changed to a sight line direction 22 from the sight line direction 20 (when the rendering image is rotated), the coordinates of the voxel data are changed in the rendering by the shear warp as illustrated in FIG. 2C. That is to say, when the rendering is performed from the sight line direction 20, the respective pieces of voxel data are rearranged such that the voxel data contained in the clipping plane thickness 21 when seen from the sight line direction 22 is used.

Accordingly, in the rendering by the shear warp, for example, as indicated by arrows at both ends in FIG. 2C, the voxel data that is used for the rendering lacks in the depth direction and an interval between the pieces of voxel data are enlarged when they are rearranged, resulting in lowering of image quality in some cases. Note that the lowering of the image quality includes generation of discontinuous portions on the image and lowering of resolution, for example.

In order to prevent the lowering of the image quality, for example, it is considered that a plurality of types of voxel data having the different slice directions are prepared previously in accordance with angles or pieces of voxel data having the different slice directions are regenerated after rotation. When the plurality of types of voxel data are prepared previously, extra memory capacity is consumed and the plurality of types of voxel data should be generated for one volume data. This lacks real-time property and it is difficult to suppress lowering of the image quality efficiently.

On the other hand, when the pieces of voxel data are regenerated after the rotation, the pieces of voxel data are generated every time a user rotates the rendering image. In the rendering by the shear warp, even when the image quality is lowered, the lowering is too small to be recognized apparently in some cases depending on rendering conditions (for example, voxel data size, structure contained in the data, transparency, and clipping plane thickness). Response after the rotation operation becomes worse if the pieces of voxel data are generated every time the user rotates the rendering image and it is difficult to suppress lowering of the image quality efficiently. For coping with this, the ultrasonic diagnostic apparatus 100 in the first embodiment makes it possible to suppress lowering of the image quality efficiently with the processing by the controller 17, which will be described later.

Figure 3:
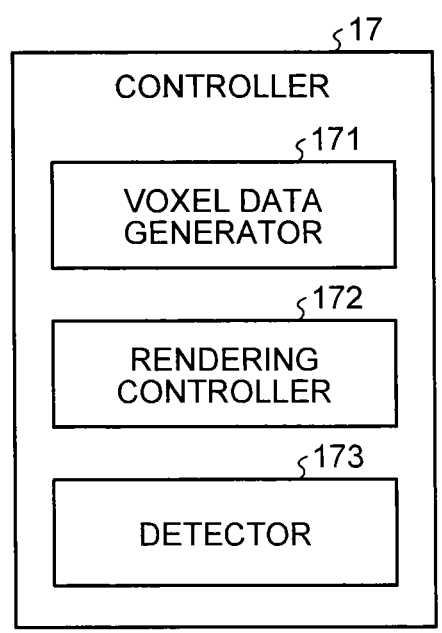
FIG. 3 is a drawing illustrating an example of a configuration of a controller in the first embodiment.

FIG. 3 is a drawing illustrating a configuration of the controller 17 in the first embodiment. As illustrated in FIG. 3, the controller 17 in the first embodiment includes a voxel data generator 171, a rendering controller 172, and a detector 173.

Figure 4A:
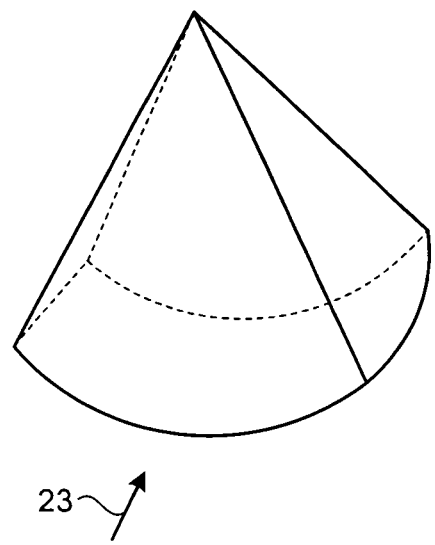
FIGS. 4A and 4B are drawings for explaining an example of voxel data generation by a voxel data generator in the first embodiment.
Figure 4B:
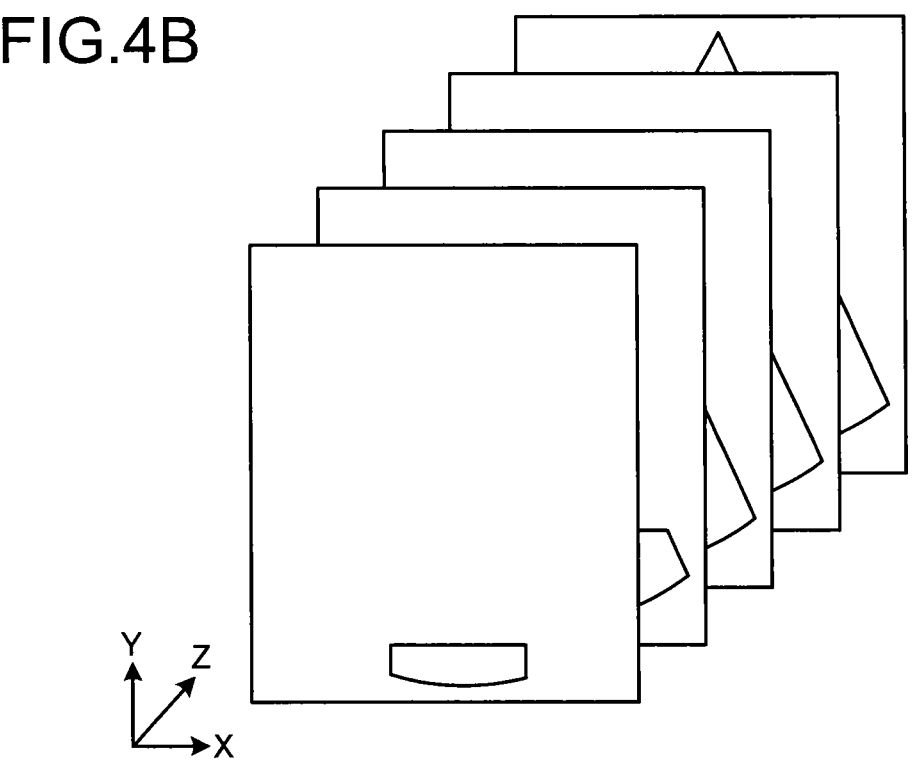

The voxel data generator 171 generates voxel data obtained by converting coordinates of the volume data into those in the three-dimensional Cartesian coordinate system. To be specific, the voxel data generator 171 generates voxel data by converting coordinates of the volume data generated by the image generator 14 into XYZ coordinates by voxel export. FIGS. 4A and 4B are drawings for explaining an example of generation of the voxel data by the voxel data generator 171 in the first embodiment.

For example, the voxel data generator 171 slices volume data as illustrated in FIG. 4A in the direction of an arrow 23 so as to generate voxel data in which respective slices are arranged on the XYZ coordinates as illustrated in FIG. 4B.

Furthermore, the voxel data generator 171 regenerates voxel data based on a determination result by the detector 173, which will be described later. In other words, the voxel data generator 171 rearranges voxel data constituting the three-dimensional data in accordance with the image quality information detected by the detector 173 based on the sight line direction. Note that the regeneration of the voxel data will be described in detail later.

Returning to FIG. 3, the rendering controller 172 divides the three-dimensional data constituted by the voxel data into a plurality of slice regions, rearranges the slice regions based on the sight line direction in which the user observes the voxel data, performs volume rendering on the voxel data in which the slice regions have been rearranged so as to generate image data. To be specific, the rendering controller 172 controls the image generator 14 to execute the volume rendering by the shear warp by using the voxel data generated by the voxel data generator 171 and generate a rendering image.

The detector 173 detects image quality information indicating image quality of the image data that is generated by the rendering controller 172. To be specific, the detector 173 acquires brightness information on the rendering image generated by the rendering controller 172 linearly and determines whether image quality of the rendering image is lowered based on the acquired brightness information. To be more specific, the detector 173 performs the Fourier transform on a waveform formed by the brightness information acquired linearly and determines that the image quality of the rendering image is lowered when a predetermined frequency component is contained. Furthermore, the detector 173 performs the Fourier transform on the waveform formed by the brightness information acquired linearly and determines that the image quality of the rendering image is lowered when no frequency component higher than a predetermined frequency is contained.

Figure 5A:
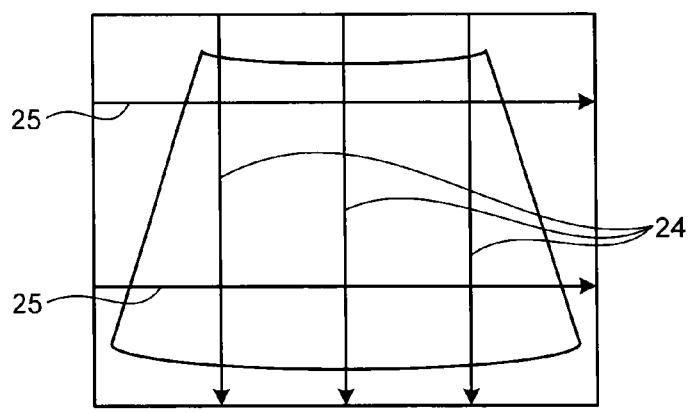
FIG. 5A is a drawing for explaining an example of processing by a detector in the first embodiment.
Figure 5B:
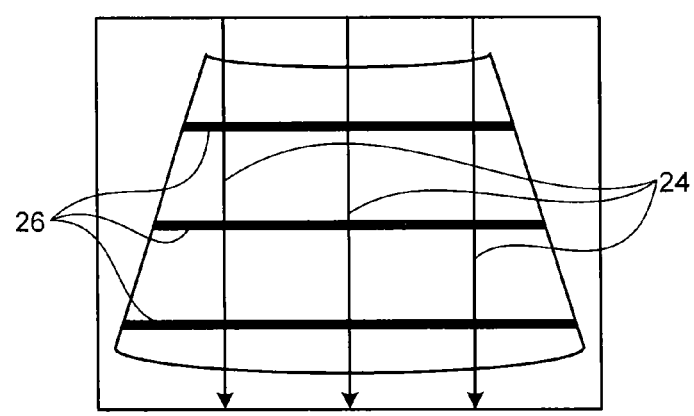
FIG. 5B is a drawing for explaining an example of processing by the detector in the first embodiment.
Figure 5C:
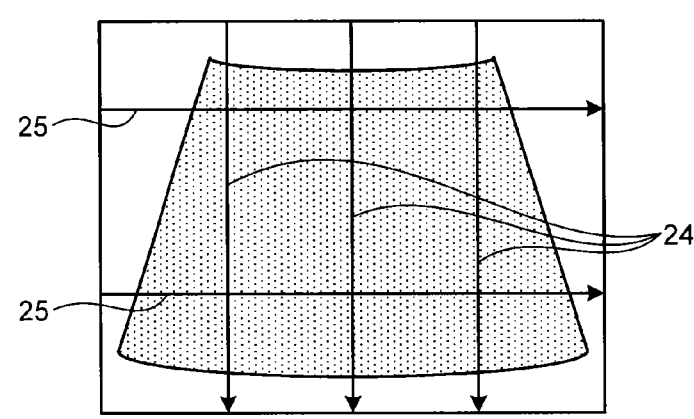
FIG. 5C is a drawing for explaining an example of processing by the detector in the first embodiment.

FIG. 5A to FIG. 5C are drawings for explaining an example of the processing by the detector 173 in the first embodiment. FIG. 5A to FIG. 5C illustrate the rendering image generated by the image generator 14 under control by the rendering controller 172. That is to say, FIG. 5A to FIG. 5C illustrate processing on the rendering image generated by the shear warp.

For example, as illustrated in FIG. 5A, the detector 173 performs sampling of brightness information for the rendering image linearly for three lines in the direction of arrows 24 and for two lines in the direction of arrows 25. The directions and the number of lines for the sampling can be set arbitrarily. The detector 173 can also determine the sampling directions based on the rendering conditions. That is to say, the detector 173 predicts the direction of a discontinuous portion that is generated on the rendering image in accordance with the rotating direction when the rendering image is rotated and executes sampling in the direction orthogonal to the predicted direction.

Then, the detector 173 analyzes the waveform formed from the brightness information sampled linearly so as to determine whether the image quality of the rendering image is lowered. For example, the detector 173 performs the Fourier transform on the waveform of the brightness information sampled linearly and determines that the rendering image contains the discontinuous portion when there is a component having an extremely high intensity at a predetermined frequency. As an example, as illustrated in FIG. 5B, the detector 173 performs the Fourier transform on the waveform of the brightness information linearly sampled in the direction of the arrows 24 and determines that the rendering image contains discontinuous portions 26 when there are components having an extremely high intensity at the predetermined frequency.

Furthermore, the detector 173 performs the Fourier transform on the waveform of the brightness information sampled linearly and determines that the resolution of the rendering image is lowered when there is no frequency component higher than the predetermined frequency. As an example, as illustrated in FIG. 5O, the detector 173 performs the Fourier transform on the waveform of the brightness information sampled linearly in the direction of the arrows 24 or the direction of the arrows 25 and determines that the resolution of the rendering image is lowered when no high frequency component is contained.

The voxel data generator 171 switches a first mode in which the voxel data used for detection by the detector 173 is output to the rendering controller 172 and a second mode in which the rearranged voxel data is output to the rendering controller 172 based on the image quality information. To be specific, when the detector 173 determines that the image quality of the rendering image generated from the voxel data is not lowered, the voxel data generator 171 outputs the voxel data to the rendering controller 172. On the other hand, when detector 173 determines that the image quality of the rendering image generated from the voxel data is lowered, the voxel data generator 171 regenerates voxel data from the volume data and outputs the regenerated voxel data to the rendering controller 172.

When the detector 173 determines that the image quality of the rendering image is lowered and the voxel data is regenerated, the voxel data generator 171 generates voxel data from the volume data based on the sight line direction. To be specific, the voxel data generator 171 regenerates the voxel data from the volume data based on the sight line direction of the volume rendering by the shear warp that is executed under control by the rendering controller 172.

Figure 6A:
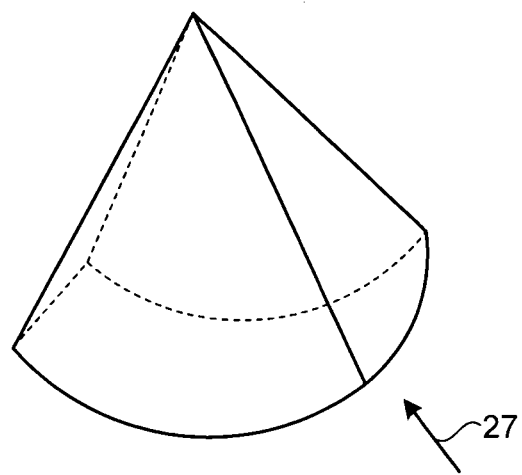
FIGS. 6A and 6B are drawings for explaining an example of voxel data regeneration by the voxel data generator in the first embodiment.
Figure 6B:
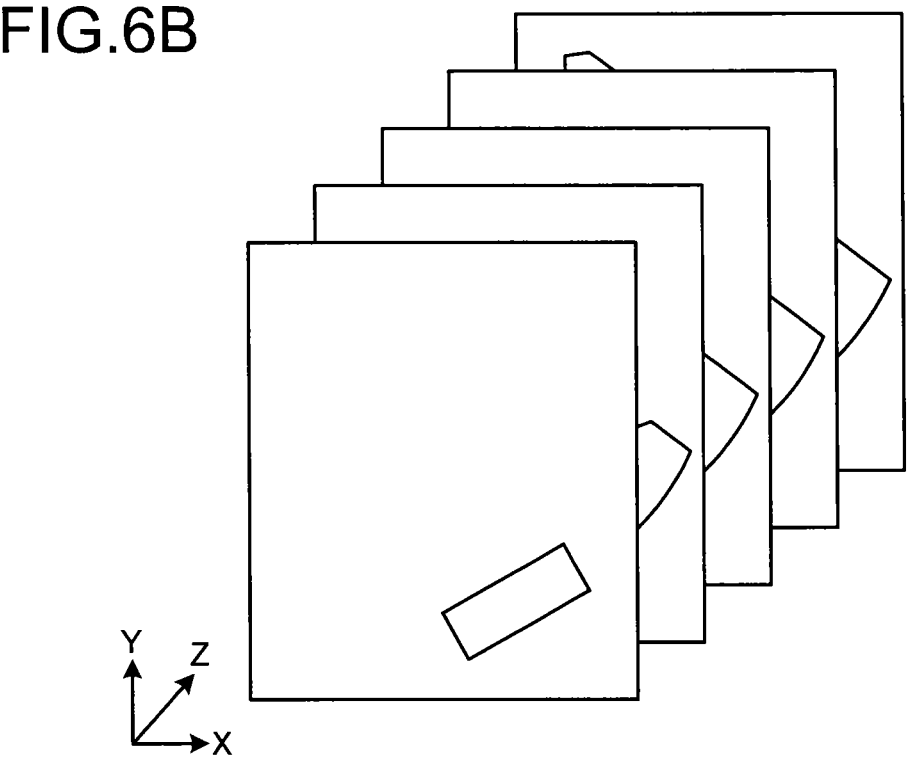

FIGS. 6A and 6B are drawings for explaining an example of voxel data regeneration by the voxel data generator 171 in the first embodiment. FIGS. 6A and 6B illustrate the voxel data regeneration from the volume data as illustrated in FIGS. 4A and 4B. For example, the voxel data generator 171 changes the slicing direction to the direction of an arrow 27 as illustrated in FIG. 6A. Then, the voxel data generator 171 slices the volume data in the direction of the arrow 27 and generates voxel data in which respective slices are arranged on the XYZ coordinates, as illustrated in FIG. 6B.

The voxel data generator 171 determines the slicing direction based on the rendering conditions of the shear warp by the rendering controller 172. That is to say, the voxel data generator 171 determines the direction in which the volume data is sliced in accordance with the rotating angle (sight line direction with respect to the volume data) of the rendering image.

When the voxel data generator 171 regenerates the voxel data, the rendering controller 172 controls the image generator 14 to execute rendering by the shear warp on the regenerated voxel data and generate a rendering image.

As described above, the controller 17 in the first embodiment determines whether image quality is lowered on the rendering image generated by the shear warp. When the controller 17 determines that the image quality is lowered, the voxel data is regenerated. With this, the ultrasonic diagnostic apparatus 100 in the first embodiment makes it possible to suppress regeneration of the voxel data to the minimum necessary and suppress lowering of the image quality of the rendering image efficiently.

Next, described is the processing of the ultrasonic diagnostic apparatus 100 in the first embodiment with reference to FIG. 7. FIG. 7 is a flowchart illustrating procedures of the processing by the ultrasonic diagnostic apparatus 100 in the first embodiment. As illustrated in FIG. 7, when the ultrasonic diagnostic apparatus 100 in the first embodiment is in a mode of rendering by the shear warp (Yes at S101), the voxel data generator 171 generates voxel data from volume data generated by the image generator 14 (S102).

The rendering controller 172 controls the image generator 14 to execute rendering by the shear warp on the voxel data generated by the voxel data generator 171 (S103). Then, when the input device 3 receives a rotation operation of the rendering image by the operator (Yes at S104), the rendering controller 172 controls to generate a rendering image after rotation.

Subsequently, the detector 173 performs sampling linearly on the generated rendering image after the rotation (S105) and executes waveform analysis by the Fourier transform (S106). To be specific, the detector 173 performs sampling of brightness information of the rendering image after the rotation linearly and performs the Fourier transform on a waveform formed by the sampled brightness information. Then, the detector 173 determines whether the rendering image contains a discontinuous portion based on a frequency obtained by the Fourier transform (S107), and further determines whether the resolution is lowered (S108).

When the detector 173 determines that the rendering image contains no discontinuous portion (No at S107) and that the resolution of the rendering image is not lowered (No at S108), the controller 17 controls to display the rendering image after the rotation on the monitor 2 (S109).

On the other hand, when the detector 173 determines that the rendering image contains the discontinuous portion (Yes at S107) or that the resolution of the rendering image is lowered (Yes at S108), the voxel data generator 171 regenerates voxel data (S110). Then, the rendering controller 172 controls the image generator 14 to execute rendering by the shear warp by using the regenerated voxel data (S111). Thereafter, the controller 17 controls to display the rendering image generated from the regenerated voxel data on the monitor 2 (S109).

Then, when the controller 17 receives a termination command (Yes at S112), the controller 17 finishes the processing. The controller 17 is in a reception standby state for the rotation operation in a state where the rendering image (image data) is displayed until it receives the termination command (No at S112). When the controller 17 does not receive the rotation operation at S104 (No at S104), the controller 17 controls to keep displaying the rendering image (image data). When the ultrasonic diagnostic apparatus 100 is not in the mode of rendering by the shear warp (No at S101), the controller 17 controls the image generator 14 to execute volume rendering (S113) and display the rendering image on the monitor 2 (S109).

As described above, according to the first embodiment, the rendering controller 172 divides the three-dimensional data constituted by the voxel data into a plurality of slice regions, rearranges the slice regions based on the sight line direction in which the user observes the voxel data, and performs volume rendering on the voxel data in which the slice regions have been rearranged so as to generate image data. The detector 173 detects image quality information indicating image quality of the image data generated by the rendering controller 172. The voxel data generator 171 rearranges voxel data constituting the three-dimensional data in accordance with the image quality information detected by the detector 173 based on the sight line direction. With this, the ultrasonic diagnostic apparatus 100 in the first embodiment makes it possible to suppress regeneration of the voxel data to the minimum necessary and suppress lowering of the image quality of the rendering image efficiently.

According to the first embodiment, the voxel data generator 171 switches the first mode in which the voxel data used for detection by the detector 173 is output to the rendering controller 172 and the second mode in which the voxel data rearranged by the voxel data generator 171 is output to the rendering controller 172 based on the image quality information. With this, the ultrasonic diagnostic apparatus 100 in the first embodiment makes it possible to determine whether to rearrange the voxel data in accordance with the image quality.

According to the first embodiment, the detector 173 acquires brightness information on the rendering image generated by the rendering controller 172 linearly and determines whether image quality of the rendering image is lowered based on the acquired brightness information. With this, the ultrasonic diagnostic apparatus 100 in the first embodiment makes it possible to determine lowering of the image quality of the rendering image with high accuracy without giving a processing load.

According to the first embodiment, the detector 173 performs the Fourier transform on the waveform formed by the brightness information acquired linearly and determines that the image quality of the rendering image is lowered when a predetermined frequency component is contained. With this, the ultrasonic diagnostic apparatus 100 in the first embodiment makes it possible to detect the lowering of the image quality when the rendering image contains the discontinuous portion.

According to the first embodiment, the detector 173 performs the Fourier transform on the waveform formed by the brightness information acquired linearly and determines that the image quality of the rendering image is lowered when no frequency component higher than a predetermined frequency is contained. With this, the ultrasonic diagnostic apparatus 100 in the first embodiment makes it possible to detect the lowering of the image quality when the resolution of the rendering image is lowered.

The first embodiment above describes the case where the Fourier transform is performed on the waveform so as to determine whether image quality is lowered. The second embodiment describes the case where whether image quality is lowered is determined based on distribution of brightness values. The ultrasonic diagnostic apparatus in the second embodiment is different from the ultrasonic diagnostic apparatus 100 in the first embodiment in only processing contents of the detector 173 as illustrated in FIG. 3. Hereinafter, described are the processing contents mainly.

The detector 173 in the second embodiment determines that image quality of a rendering image is lowered when distribution of brightness values of the brightness information acquired linearly is in a predetermined range. To be specific, the detector 173 generates a histogram of the respective brightness values of the brightness information acquired linearly and determines that a resolution of the rendering image is lowered when the distribution of the brightness values is in the predetermined range.

Next, described is processing of the ultrasonic diagnostic apparatus 100 in the second embodiment with reference to FIG. 8. FIG. 8 is a flowchart illustrating procedures of the processing by the ultrasonic diagnostic apparatus 100 in the second embodiment. As illustrated in FIG. 8, when the ultrasonic diagnostic apparatus 100 in the second embodiment is in a mode of rendering by the shear warp (Yes at S201), the voxel data generator 171 generates voxel data from volume data generated by the image generator 14 (S202).

The rendering controller 172 controls the image generator 14 to execute rendering by the shear warp on the voxel data generated by the voxel data generator 171 (S203). Then, when the input device 3 receives a rotation operation of the rendering image by the operator (Yes at S204), the rendering controller 172 controls to generate a rendering image after rotation.

Subsequently, the detector 173 performs sampling linearly on the generated rendering image after the rotation (S205) and executes waveform analysis by the Fourier transform (S206). To be specific, the detector 173 performs sampling of brightness information of the rendering image after the rotation linearly and performs the Fourier transform on a waveform formed by the sampled brightness information. Then, the detector 173 determines whether the rendering image contains a discontinuous portion based on a frequency obtained by the Fourier transform (S207)

Thereafter, the detector 173 executes waveform analysis by pixel count (S208). To be specific, the detector 173 determines whether a resolution of the rendering image is lowered based on the distribution of the brightness values of the brightness information sampled linearly (S209)

When the detector 173 determines that the rendering image contains no discontinuous portion (No at S207) and the resolution of the rendering image is not lowered (No at S209), the controller 17 controls to display the rendering image after the rotation on the monitor 2 (S210).

On the other hand, when it is determined that the rendering image contains the discontinuous portion (Yes at S207) or the resolution of the rendering image is lowered (Yes at S209), the voxel data generator 171 regenerates voxel data (S211). Then, the rendering controller 172 controls the image generator 14 to execute rendering by the shear warp by using the regenerated voxel data (S212). Thereafter, the controller 17 controls to display the rendering image generated from the regenerated voxel data on the monitor 2 (S210).

Then, when the controller 17 receives a termination command (Yes at S213), the controller 17 finishes the processing. The controller 17 is in a reception standby state for the rotation operation in a state where the rendering image (image data) is displayed until it receives the termination command (No at S213). When the controller 17 does not receive the rotation operation at S204 (No at S204), the controller 17 controls to keep displaying the rendering image (image data). When the ultrasonic diagnostic apparatus 100 is not in the mode of rendering by the shear warp (No at S201), the controller 17 controls the image generator 14 to execute volume rendering (S214) and display the rendering image on the monitor 2 (S210).

As described above, according to the second embodiment, the detector 173 determines that the image quality of the rendering image is lowered when distribution of the brightness values of the brightness information acquired linearly is in a predetermined range. With this, the ultrasonic diagnostic apparatus 100 in the second embodiment makes it possible to easily detect lowering of the image quality when the resolution of the rendering image is lowered.

The first and the second embodiments above describe the case where the rendering image after rotation is generated, sampling of the brightness information of the generated rendering image is performed linearly, and it is determined whether the image quality is lowered based on the sampled brightness information. The third embodiment describes the case where lowering of image quality is predicted based on rendering conditions after rotation.

FIG. 9 is a drawing illustrating an example of a configuration of the controller 17 in the third embodiment. As illustrated in FIG. 9, the controller 17 in the third embodiment further includes an image quality prediction unit 174 newly. The image quality prediction unit 174 predicts whether the image quality of the rendering image is lowered based on conditions of volume rendering that is executed by the rendering controller 172. To be specific, the image quality prediction unit 174 predicts whether the image quality of the rendering image after the rotation is lowered based on the prediction information stored by the internal storage unit 16.

Described is the prediction information. FIG. 10 is a table illustrating an example of the prediction information stored by the internal storage unit 16 in the third embodiment. For example, as illustrated in FIG. 10, the internal storage unit 16 stores therein the prediction information in which respective conditions are associated with values as determination references. As an example, the internal storage unit 16 stores therein the prediction information in which respective rendering conditions such as a "voxel data size", a "display range", "transparency", a "rotating angle", and a "clipping plane thickness" are associated with the values.

The image quality prediction unit 174 acquires information of operation contents such as the rotating angle and rendering conditions by the shear warp that are controlled by the rendering controller 172 when the input device 3 receives the rotation operation by the operator. Then, the image quality prediction unit 174 compares the respective pieces of acquired information and the prediction information so as to determine whether the image quality of the rendering image is lowered. For example, the image quality prediction unit 174 compares values of the pieces of acquired information and values of the prediction information for the respective conditions so as to determine whether the image quality of the rendering image is lowered. The conditions contained in the prediction information and the values for the respective conditions are determined arbitrarily. The prediction may be performed by using only one condition or the prediction may be performed by using a plurality of conditions.

When the image quality prediction unit 174 determines that the image quality of the rendering image is not lowered, the voxel data generator 171 outputs the voxel data that has been already generated to the rendering controller 172. On the other hand, when the image quality prediction unit 174 determines that the image quality of the rendering image is lowered, the voxel data generator 171 regenerates voxel data based on the rendering conditions and outputs the regenerated voxel data to the rendering controller 172.

Next, described is processing by the ultrasonic diagnostic apparatus 100 in the third embodiment with reference to FIG. 11. FIG. 11 is a flowchart illustrating procedures of the processing by the ultrasonic diagnostic apparatus 100 in the third embodiment. As illustrated in FIG. 11, when the ultrasonic diagnostic apparatus 100 in the third embodiment is in a mode of rendering by the shear warp (Yes at S301), the voxel data generator 171 generates voxel data from the volume data generated by the image generator 14 (S302).

The image quality prediction unit 174 acquires rendering conditions by the shear warp that is executed by the rendering controller 172 (S303) and determines whether the image quality of the rendering image is lowered. To be specific, the image quality prediction unit 174 predicts whether the rendering image contains a discontinuous portion (S304) and predicts whether the resolution is lowered (S305).

When it is predicted that the discontinuous portion is not generated on the rendering image (No at S304) and the resolution of the rendering image is not lowered (No at S305), the rendering controller 172 controls the image generator 14 to execute rendering by the shear warp on the voxel data generated by the voxel data generator 171 (S307). Then, the controller 17 controls to display the rendering image (image data) on the monitor 2 (S308).

On the other hand, when it is predicted that the discontinuous portion is generated on the rendering image (Yes at S304) or the resolution of the rendering image is lowered (Yes at S305), the voxel data generator 171 regenerates the voxel data (S306). Then, the rendering controller 172 controls the image generator 14 to execute the rendering by the shear warp by using the regenerated voxel data (S307). Thereafter, the controller 17 controls to display the rendering image generated from the regenerated voxel data on the monitor 2 (S308).

Then, when the input device 3 receives the rotation operation of the rendering image by the operator (Yes at S309), the image quality prediction unit 174 acquires information of the rotation operation. In addition, the process returns to S303 and the image quality prediction unit 174 executes prediction whether the image quality is lowered, again.

Then, when the controller 17 receives a termination command (Yes at S310), the controller 17 finishes the processing. The controller 17 is in a reception standby state for the rotation operation in a state where the rendering image (image data) is displayed until it receives the termination command (No at S310). When the controller 17 does not receive the rotation operation at S309 (No at S309), the controller 17 controls to keep displaying the rendering image (image data). When the ultrasonic diagnostic apparatus 100 is not in the mode of rendering by the shear warp (No at S301), the controller 17 controls the image generator 14 to execute volume rendering (S311) and display the rendering image on the monitor 2 (S308).

As described above, in the ultrasonic diagnostic apparatus 100 in the third embodiment, the image quality prediction unit 174 predicts whether the image quality of the rendering image is lowered based on the conditions of the volume rendering that is executed by the rendering controller 172. With this, the ultrasonic diagnostic apparatus 100 in the third embodiment makes it possible to omit generation of the rendering image by the shear warp so as to reduce the processing load.

Although the first, second, and third embodiments have been described, the embodiment may be executed in various different modes other than the first, the second, and the third embodiments described above.

In the first and the second embodiments described above, sampling is performed linearly from the rendering image. Note that the embodiment is not limited thereto and sampling may be performed on a predetermined region, for example.

In the first and the second embodiments described above, the discontinuous portion on the image is detected by the Fourier transform. The embodiment is not limited thereto and the detection of the discontinuous portion can be executed by an arbitrary algorithm.

Furthermore, in the first to the third embodiments described above, image quality is determined when the discontinuous portion is contained or when the resolution is lowered and the voxel data is regenerated. Note that the embodiment is not limited thereto and the image quality may be determined comprehensively, for example. As an example, the degree that the predetermined frequency component is contained and the degree that the high frequency component lacks may be set in stages and it may be determined whether the voxel data is regenerated based on the respective determination results.

The first to the third embodiments above describe the case where the ultrasonic diagnostic apparatus determines the image quality of the rendering image and regenerates the voxel data when it is determined that the image quality is lowered. Alternatively, the above-mentioned processing may be executed by an image processing apparatus such as a workstation. In such a case, for example, the workstation connected to an ultrasonic diagnostic apparatus or an image storage apparatus through a network acquires volume data from the ultrasonic diagnostic apparatus or the image storage apparatus. Then, the workstation executes the above-mentioned processing by using the acquired volume data.

As described above, with the first embodiment, the second embodiment, the third embodiment, and the fourth embodiment, the ultrasonic diagnostic apparatus, the image processing apparatus, and the image processing method in the embodiments make it possible to suppress lowering of the image quality efficiently.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
   a rendering unit that divides three-dimensional data constituted by voxel data into a plurality of slice regions, rearranges the slice regions based on a sight line direction in which the voxel data is observed, and performs volume rendering on the voxel data in which the slice regions have been rearranged so as to generate image data;
   a detector that detects image quality information indicating image quality of image data that is generated by the rendering unit; and a voxel data generator that rearranges the voxel data constituting the three-dimensional data in accordance with the image quality information detected by the detector based on the sight line direction wherein the detector determines whether the image quality is lowered based on acquired brightness information.

2. The ultrasonic diagnostic apparatus according to claim 1, wherein the voxel data generator switches a first mode in which the voxel data used for detection by the detector is output to the rendering unit and a second mode in which the voxel data rearranged by the voxel data generator is output to the rendering unit.

3. The ultrasonic diagnostic apparatus according to claim 1, wherein the detector performs Fourier transform on a waveform formed by the brightness information acquired linearly and determines that the image quality of the image data is lowered when a predetermined frequency component is contained.

4. The ultrasonic diagnostic apparatus according to claim 1, wherein the detector performs Fourier transform on a waveform formed by the brightness information acquired linearly and determines that the image quality of the image data is lowered when no frequency component higher than a predetermined frequency is contained.

5. The ultrasonic diagnostic apparatus according to claim 1, wherein the detector determines that the image quality of the image data is lowered when distribution of brightness values of the brightness information acquired linearly is in a predetermined range.

6. An image processing apparatus comprising:

a rendering unit that divides three-dimensional data constituted by voxel data into a plurality of slice regions, rearranges the slice regions based on a sight line direction in which the voxel data is observed, and performs volume rendering on the voxel data in which the slice regions have been rearranged so as to generate image data;

a detector that detects image quality information indicating image quality of image data that is generated by the rendering unit; and a voxel data generator that rearranges the voxel data constituting the three-dimensional data in accordance with the image quality information detected by the detector based on the sight line direction wherein the detector determines whether the image quality is lowered based on acquired brightness information.

7. An image processing method that is executed by an image processing apparatus, the image processing method comprising: dividing three-dimensional data constituted by voxel data into a plurality of slice regions, rearranging the slice regions based on a sight line direction in which the voxel data is observed, and performing volume rendering on the voxel data in which the slice regions have been rearranged so as to generate image data; detecting image quality information indicating image quality of image data that is generated in the volume rendering; and rearranging the voxel data constituting the three-dimensional data in accordance with the detected image quality information based on the sight line direction wherein the detector determines whether the image quality is lowered based on acquired brightness information.

* * * * *